US008618035B2

(12) United States Patent
Lai et al.

(10) Patent No.: US 8,618,035 B2

(45) Date of Patent: Dec. 31, 2013

(54) SOAP BAR CONTAINING HYDROGEL PHASE PARTICLES

(75) Inventors: Mac Lai, Shanghai (CN); Jayprakash Vidwans, Mumbai (IN); Qian Wu, Shanghai (CN)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 245 days.

(21) Appl. No.: 12/568,741

(22) Filed: Sep. 29, 2009

(65) Prior Publication Data

US 2011/0077186 A1 Mar. 31, 2011

(51) Int. Cl.
*A61K 8/00* (2006.01)

(52) U.S. Cl.
USPC ............ 510/141; 510/152; 510/153; 510/155

(58) Field of Classification Search
None
See application file for complete search history.

(56) References Cited

U.S. PATENT DOCUMENTS

| | | | |
|---|---|---|---|
| 2,677,665 A | 5/1954 | James et al. | |
| 4,820,447 A | 4/1989 | Medcalf et al. | |
| 5,703,026 A | 12/1997 | Setser et al. | |
| 6,310,016 B1 | 10/2001 | Behal et al. | |
| 6,440,908 B2 | 8/2002 | Racherla | |
| 7,285,521 B2 | 10/2007 | Chakrabarty et al. | |
| 2005/0276828 A1 | 12/2005 | Grissett et al. | |
| 2010/0008884 A1* | 1/2010 | Brandt et al. | 424/70.16 |
| 2010/0215700 A1* | 8/2010 | Moaddel et al. | 424/401 |

FOREIGN PATENT DOCUMENTS

WO WO 2007/146027 12/2007

OTHER PUBLICATIONS

Melvita Algascience Exfoliating Bath Soap, [package] UK, Melvita, Available since at least 2011.
Mustika Ratu Kipi body Soap, [package] Indonesia, Mustika Ratu , Available since at least 2011.
Faberlic Collection Polyneisie Peeling Soap, [package] Russia, Faberlic, Available since at least 2011.
Scarlett Algae Bar Soap, [package] France, Cyra Lydo, Available since at least 2011.
Aquascience Ban & Douche Seaweed Exfoliating Soap, [package] France, Thalassa Sea & Spa, Available since at least 2011.
Kels Fresh Spirulina Honey Beauty Soap, [package] Malaysia, I Medikel Pharmaceutical, Available since at least 2011.
BodyFarm Exfoliating Soap Bar, [package] Greece, odyfarm Hellas, Available since at least 2010.
Nuxe Body Exfoliant Soap, [package] Spain, Laboratoire Nuxe, Available since at least 2010.
Seaweed Organics Seaweed Scrub Soap Bar, [package] UK, Diana Drummond, Available since at least 2010.
Oriflame Swedish Spa Minerals Scrub Bar, [package] India, Oriflame, Available since at least 2009.
The Body Shop Gently Purify Radiance Boosting Sisal Cleanser, [package] Singapore, The Body Shop, Available since at least 2008.
Seaderm Exfoliating Soap, [package] France, Seaderm France, Available since at least 2008.
Melvita Slimming Bar Soap, [package] Finland, Melvita, Available since at least 2008.
Phytomer Seaweed Soap, [package] USA, Phytomer, Available since at least 2007.

(Continued)

*Primary Examiner* — Necholus Ogden, Jr.

(57) ABSTRACT

A millable solid soap. The millable solid soap contains a solid phase soap base and hydrogel phase particles dispersed in said soap base. The hydrogel phase particles act as fillers to render a low total fatty matter solid soap.

9 Claims, 1 Drawing Sheet

(56) References Cited

OTHER PUBLICATIONS

Confianca O Melhor Exfoliating Soap, [package] France, Saboaria Perfumaria Confianca, Available since at least 2007.
Wellness & Beauty by Sandro Lorenzo Magnolie & Olive Soap Bar, [package] Germany, Rossman, Available since at least 2007.
Every Man Jack Body Bar with Glycerin, [package] USA, Every Man Jack, Available since at least 2007.
Algascience Red Seaweed Exfoliating Bath Soap, [package] Belgium, Melvitacosm, Available since at least 2002.
The Body Shop Seaweed & Loofah Exfoliating Bar, [package] Finland, The Body Shop, Available since at least 2001.
Melvita Algascience Exfoliating Bath Soap, UK, Available since at least 2011.
Mustika Ratu Kipi body Soap, Indonesia, Available since at least 2011.
Faberlic Collection Polyneisie Peeling Soap, Russia, Available since at least 2011.
Scarlett Algae Bar Soap, France, Available since at least 2011.
Aquascience Ban & Douche Seaweed Exfoliating Soap, France, Available since at least 2011.
Kels Fresh Spirulina Honey Beauty Soap, Malaysia, Available since at least 2011.
BodyFarm Exfoliating Soap Bar, Greece, Available since at least 2010.
Nuxe Body Exfoliant Soap, Spain, Available since at least 2010.
Seaweed Organics Seaweed Scrub Soap Bar, UK, Available since at least 2010.
Oriflame Swedish Spa Minerals Scrub Bar, India, Available since at least 2009.
The Body Shop Gently Purify Radiance Boosting Sisal Cleanser, Singapore, Available since at least 2008.
Seaderm Exfoliating Soap, France, Available since at least 2008.
Melvita Slimming Bar Soap, Finland, Available since at least 2008.
Phytomer Seaweed Soap, USA, Available since at least 2007.
Confianca O Melhor Exfoliating Soap, France, Available since at least 2007.
Wellness & Beauty by Sandro Lorenzo Magnolie & Olive Soap Bar, Germany, Available since at least 2007.
Every Man Jack Body Bar with Glycerin, USA, Available since at least 2007.
Algascience Red Seaweed Exfoliating Bath Soap, Belgium, Available since at least 2002.
The Body Shop Seaweed & Loofah Exfoliating Bar, Finland, Available since at least 2001.
European Search Report dated Aug. 3, 2011 for corresponding EPA No. 10251665.5.

* cited by examiner

SOAP BAR CONTAINING HYDROGEL PHASE PARTICLES

TECHNICAL FIELD

This invention relates to a cleansing soap bar. In particular, the invention relates to a low total fatty mater (TFM) cleansing soap bar having acceptable properties to consumers, particularly bars made by amalgamating, milling, extruding and stamping.

BACKGROUND

Traditional soap bars are made from soap noodles, with 70 wt % or more of total fatty material (TFM), 10-14 wt % water, and include other additives (such as titanium dioxide, surfactant and fragrance). These bars are mainly produced by mixing the soap noodles with other additives, followed by milling, extruding and stamping processes.

Generally, traditional soaps are alkali (usually sodium) salts of fatty acids from oils or fats, which can come be of animal and/or plant origin. Common sources of oils and fats are, for example, palm oil, palm kernel oil, coconut oil, cattle tallow, sheep tallow, lard, and other similar oils and fats from other organisms. Fats and oils contain in substantial part glycerides of varying chain lengths, which are esters of glycerol (glycerin) and fatty acids. Under alkaline conditions and heat, the glycerides in the fats and oils form glycerin and fatty acid salts, also known as soaps.

Commercially, soaps are made by adding additives to soap noodles and further processing the mixture into soap. Soap noodles are typically made from oil or fat of blends thereof by three methods commonly known in the art. One method is the direct saponification of oil/fat in which the oil/fat is reacted with an alkali (typically sodium hydroxide) to form glycerin and the soap base (which contains fatty acid alkali salt, e.g., fatty acid sodium salt, which is also carboxylic acid sodium salt). The soap base is the fatty-acid-alkali-salt-containing material that is to be used for forming soap by adding fillers, fragrance, and other additives. Thus, the material after removal of glycerin (if glycerin is to be removed) and to be further processed is an example of soap base. Another method of making soap involves the neutralization of fatty acid with the alkali (e.g., NaOH) to form the soap base. In the soap-making process, the soap base can be dried and plodded into noodles or chips. As used herein, the term "soap noodles" refers to the pellets or pieces of soap (whether they be in pellet, chip, bits, or other shapes). Soap noodles are typically the result of the drying and extruding of raw soap into unit form such that the soap units or pieces can be further processed into the finished soap bars by mixing with additives, as known to those skilled in the art of soap making. The soap noodle contains the soap base and can optionally contain other materials such as glycerin. Cleansing soap bars are mostly produced by mixing the soap noodles with additives, such as fragrance, fillers, etc., followed by milling, extruding and stamping processes.

Traditionally, finished milled soap bars include soap noodle TFM of more than 70 wt %, 10-14 wt % water, and other additives (such as titanium dioxide, surfactant and fragrance). At the present, milled bars generally have a water content of about 8-15 wt % and hard non-milled bars have a water content of about 20-35 wt %. Hard non-milled bars can contain moisture of less than 35 wt %. Such non-milled bars have a TFM of about 30-65 wt %. The reduction in TFM traditionally is done by including insoluble particulate materials and/or soluble silicates in the soap bars. Such non-milled bars are generally quite soft and subjecting the soap bars to the milling process will cause water to separate out.

Generally, fillers are used as soap noodle replacement in soap formulation design. For example, commonly used fillers include kaolin, talc and other inorganic mineral fillers. More than 16 wt % of kaolin can be used in the soap formulation with the acceptable properties and kaolin might reduce the feeling of greasiness on the skin. Other materials that have been added in the making of soap include silica gel, sodium aluminate, and borate compounds. In some cases, water absorbing materials are added in soap-making to increase the content of water. Examples of patent documents related to soaps that have water absorbing material include US 20050276828A and WO2007146027. Examples of patent documents that are related to adding fillers or including water absorbing material in the soap making process include U.S. Pat. Nos. 2,677,665, 5,703,026, 6,310,016, 6,440,908, and 7,285,521.

However, the inclusion of a large amount of water or fillers into the soap bar not only may affect the cleansing and sensory feel of the soap, but often also adversely affect the processing conditions. There continues to be a need for improved soap bars with an increased amount of water or fillers wherein the soap bars are able to provide effective cleansing property with lowered TFM.

SUMMARY

The present invention provides a method and a soap bar having hydrogel fillers, which can be a coreless composite. Preferably, the hydrogel fillers are in a hydrogel phase composite and includes polyols or powders. With the inclusion of powdery material in the hydrogel phase of the filler, the filler is a composite because it is made from two or more constituent materials with significantly different physical or chemical properties. The two or more constituent materials remain separate and distinct on a macroscopic level within the finished structure. Inclusion of this unique hydrogel phase in the soap structure leads to new soaps and new soap-making processes, leading to performance enhancement beneficial to the consumers. The present invention also relates to methods of making soap bar having hydrogel fillers.

In one aspect, the present invention provides a millable solid soap that contains a solid phase soap base and hydrogel phase particles dispersed in the soap base. The soap base is solid to the sensory feel of an average person and maintains its shape during packaging, storage, handling and shipping process without change in shape. Preferably, the particles of the hydrogel phase material are coreless. Preferably, the hydrogel phase particles contain polyols or powdery material and have a large amount of water therein.

In another aspect, the present invention relates to a method of making solid soap. The method of making the solid soap includes pre-forming a hydrogel liquid, charging the hydrogel liquid into the mixer at high temperature, mixing the liquid solution with soap noodles and other additives, forming the coreless hydrogel particles in-situ during mixing, and forming a soap bar. The hydrogel liquid is essentially in solution form, although if preferred, certain amount of undissolved material can be present. The forming of the coreless hydrogel particles can be followed by refining, extruding, extruding and stamping. By adjusting the ratio of components that are to be mixed to form the hydrogel particles, such components can be more easily processed into hydrogel particles, without bringing any noticeable negative effect that can be experienced by consumers.

In one aspect of the invention, a novel soap bar and technique for making a soap bar are provided for a soap bar having composite hydrogel particles containing powdery components therein.

The present invention provides formulating flexibility for soap making. With the hydrogel phase particles of the present invention, water soluble active ingredients, such as vitamin C, etc., can be added to the hydrogel phase and still the hydrogel phase particles can be stable and maintain their function until being used. Such preservation of active soluble ingredients is very difficult to achieve in traditional bars because of the limitation of 8-15 wt % of water content and the high pH value. With the hydrogel phase, more synthetic surfactants in liquid form can be added into a soap formulation, which provide another way to modify or improve soap performance. With the hydrogel phase of the present invention, the soap noodle ratio in soap can be reduced to a very low level, thereby improving the mildness of the soap. With the present hydrogel phase, glycerin, polyol, and/or other moisturizers can be easily added to the soap without causing hard-to-manage stickiness, and provides more moisturization benefit to the consumer compared to traditional soap. In contrast, generally, if more than 5 wt % glycerin or polyols are added into the formulation in the conventional bar making process, the soap noodle will become very sticky in the mixer, thereby making the mixing difficult to control and requiring a long mixing time. Similarly, when incorporating inorganic particles such as talc, the particles can be placed such that they are more concentrated in the hydrogel phase.

The present invention also provides processing benefits. The hydrogel phase of the present invention can be easily mixed with soap noodle and be processed on the traditional soap finish line. And when adding glycerin or sorbitol into the hydrogel phase, the use of hydrogel is a way to overcome the process difficulty caused by the soap noodle's stickiness compared to adding high level of glycerin in traditional soap making. Adding powdery material such as talc into the hydrogel phase also improves the compatibility of the powdery material with soap noodles to result in reduction or prevention of cracking. Thus, a higher level of such powdery material, such as talc, can be added into soap formulation with the use of hydrogel phase compared to traditional soap-making techniques.

The hydrogel phase can also act as an advantageous fragrance delivery vehicle in soap matrix and help to deliver flavor and fragrance effectively. The flavor and/or fragrance, being introduced into the soap bar by means of the hydrogel phase particulates, can be slowly released, thus providing favorable impression to the consumer.

With the inclusion of hydrogel phase fillers, which can act as soap noodle replacement, the present invention reduces the soap noodle dosage to a very low level without significant adverse impact on cleansing property. Compared to traditional soap, such a soap formulation can be made with relatively low cost.

Since the hydrogel of the present invention contain a large amount of water (in fact, it is mostly water), and the gelling materials are mostly colorless or light in color, the refractive index of the hydrogel phase particles can be adjusted to a large degree through the inclusion of polyols and adjusting the different amount of the polyols included. With transparent or translucent soap noodles, once the refractive index of the material of the hydrogel phase particles are the same or near to that of the soap noodle, the hydrogel phase particles are much less distinguishable from the soap noodle. As a result, transparent and translucent soap bars can be made with hydrogel phase fillers of the present invention.

DETAILED DESCRIPTION

The present invention relates to a soap bar having novel hydrogel fillers. Preferably the hydrogel fillers are coreless. Preferably the hydrogel fillers are composites. The present invention also relates to methods of making soap bars having hydrogel fillers. Introducing a unique hydrogel phase to the soap structure provides new flexibility for designing and making soap and also can bring other performance benefits to the consumer. In an embodiment, the soap bar of the present invention includes fillers in a hydrogel phase in particle form, preferably the particle is coreless. Such solid soap can be used for cleansing purposes as toilet soap or laundry soap, such as for cleaning hands, washing clothes, etc.

As used herein, the term "soap bar" refers to a unit of solid soap after it is made into a shape suitably stable in general commercial room condition and ready to be used. The bar may have various shapes in sectional view, such as round, oval, rectangle, square, star, etc., as known to the skilled artisans.

As used herein, the term "coreless" refers to a form of hydrogel in which a unit of hydrogel wherein the inner central part does not have a higher concentration of hydrogel gelling material (such as carrageenan) than the more peripheral regions of the unit (e.g., particle).

The term "included constituent" or "constituent included" as used herein regarding material in hydrogel refers to an ingredient, especially a nonwater material ingredient that is included in the hydrogel. Preferably, when in the finished soap bar, an included constituent is present in higher concentration in the hydrogel phase particles than in the soap matrix material outside said particles.

In describing the present invention, the following terms will be employed, and are intended to be defined as indicated below. As used in this specification and the appended claims, the singular forms "a," "an" and "the" include plural references unless the text content clearly dictates otherwise.

As used herein, the term "thermoreversible" as applied to hydrogel refers to a hydrogel that is a flowable (which can flow under gravity) sol or liquid at elevated temperature at or above 90° C. and forms a non-flowable hydrogel that has a phase surface in atmosphere at room temperature (about 25° C.) wherein the hydrogel can become flowable liquid again when heated to the elevated temperature.

The term "hydrogel solution" refers to a solution in which more than 90% of the hydrogel gelling material has been dissolved or is in colloidal form. The solution can, but need not, be a clear solution.

"Beneficial agent" is to be construed in its broadest sense to mean any material that is intended to produce some biological, beneficial, therapeutic, or other intended useful effect, such as enhancing permeation, improving sensory feel, and moisturizing.

Figure 1:
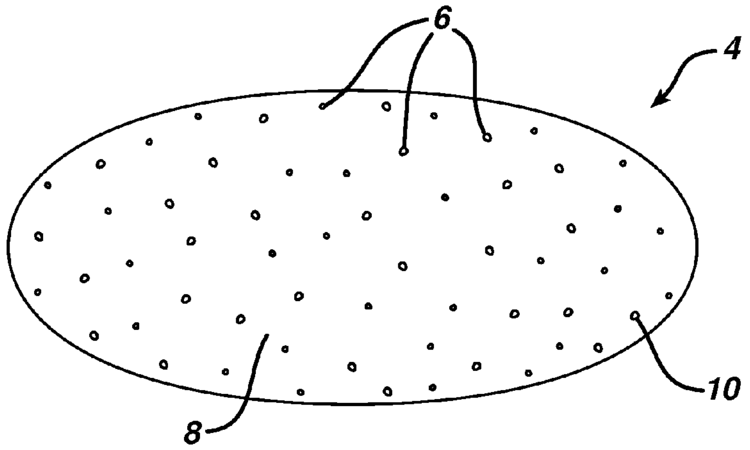
FIG. 1 is a sectional view of an embodiment of a solid soap bar of the present invention.

FIG. 1 illustrates an embodiment of a soap bar according to this invention. The solid soap bar 4 includes hydrogel phase particles 6 dispersed in soap matrix 8, which is composed of soap base material and other additives but excluding the hydrogel phase particles 6. The soap matrix is the material in which the hydrogel phase particles are embedded. The hydrogel phase particles 6 preferably have well defined phase boundary surface 10 separating the content of the hydrogel phase particles 6 from the soap base material 8. The particle surface need not be smooth, since many of the particles can be formed by breaking up larger pieces of hydrogel. Because the hydrogel solution is mixed well before gelling, the hydrogel gelling agent and water, as well other beneficial agents are evenly distributed in the hydrogel solution. As the hydrogel solution material gels and eventually forms hydrogel particles that are embedded in the matrix, the content in the hydrogel particles continue to remain in uniform or substantially uniform distribution. In the resulting soap bar, under commercial storage condition at room temperature (such as at 25° C.) even over a period of time, during which time water or other vaporizable or liquid material may diffuse away from the hydrogel phase particles into the soap matrix, the diffusion process is slow that such content materials in the hydrogel particles, except for the microscopic boundary conditions at the phase surface, would substantially be distributed evenly in the hydrogel phase particles at the vast majority of the particles. For example, constituents included in the hydrogel, such as talc and glycerin are distributed substantially uniformed within the bulk in the hydrogel phase particles (i.e., in the interior of the particle away from the boundary conditions). As used herein, the term "phase" when referred to the hydrogel particle refers to separation of hydrogel material from soap base material by a boundary of the hydrogel unit (such as a particle) in which the content material (such as water) is distributed substantially uniformly within the unit, whereas such material is present in substantially different distribution outside of the boundary. To facilitate processing, such hydrogel phase particles preferably are of a gel material having gel strength that gives a hardness to the sensory feel of the consumer at a large enough particle size (e.g., 5 μm to 2 mm diameter) the particles provides a grainy or granular feel to a consumer. Beneficial agents that can be included in the hydrogel phase particles, such as vitamins, fragrance, moisturizing agents, etc., can benefit the skin as the hydrogel phase particles come into contact with the skin. Further, such beneficial agents can migrate slowly past the phase surface boundary into the soap matrix material with time and eventually come into contact with skin to provide beneficial effect when the soap bar is used.

One of the ingredients of the solid soap bar of the present invention is fatty acid soap, which is generally provided in the form of soap noodles in the soap making process. The term of fatty acid soap denotes alkali salts of carboxylic fatty acid. The soap may be derived from any of the triglycerides conventionally used in soap manufacture. Consequently the carboxylate anions in the soap may contain from 8 to 22 carbon atoms. The fatty acid soap can be made from the usual fatty acid sources such as animal fats and vegetable oils or combinations thereof, which can include palm oil, palm kernel oil, caster oil, rice bran oil, sunflower oil, coconut oil, soybean oil, peanut oil, tallow, lard, fish oil, and blends thereof, and the like. Typical blends of palm and palm kernel oils, palm and coconut kernel oils, can be at blend ratios of about 40/60 to 97/3 of various oils and fats. As mentioned above, techniques and processes of making soap from fats and oils are well known in the art.

Generally, the fatty acid soap material (which is the same as TFM) can constitute about 40 wt % to 90 wt %, preferably about 50 wt % to 90 wt %, more preferably about 60 wt % to 80 wt %, preferably 70 wt % or less of the soap bar of the present invention. Preferably, the fatty acid soap material is provided as soap noodles, such as those made from saponification processes. The soap noodles can be mixed and further processed with hydrogel to result in the final soap bar through mixing, milling, extruding, and stamping, etc. From the soap noodle type, the TFM can be determined. Typically, the soap noodle manufacturer provides the information on the TFM of the soap noodle. For example, soap noodle of a palm and palm kernel oils blend of 80:20 has a TFM of about 82 wt %. Depending on the weight percentage of the soap noodle used in making the soap bar, the percent of TFM in the soap bar can then be calculated. Although synthetic soap bars can be made to include the hydrogel particles of the present invention, to provide physical property such that the soap can have the quality of a hard, milled bar, it is preferred that the soap bar is made from soap noodles. As used herein, the term "synthetic soap bar" refers to a soap bar that is made by molding a composition that contains synthetic surfactants and binders and rather than fatty acid alkali salt from soap noodles.

Other than sodium hydroxide and traditional natural fatty acids in or from animal fats and vegetable oils, soap can also be made from other alkali metal or alkanol ammonium alkali and alkane- or alkene monocarboxylic acids. Sodium, magnesium, potassium, calcium, mono-, di- and tri-ethanol ammonium cations, or combinations thereof can be used. The salts formed from the reaction between fatty acids and such cations are considered fatty acid alkali salts herein. The soaps can be made from fatty acids having about 8 to 22 carbon atoms, preferably about 12 to about 18 carbon atoms. The soap (such as soap noodles) forms a soap base in which hydrogel can be mixed with and processed into soap bars that have the hydrogel phase particulate material in which a significant amount of water is bound.

The present invention enables the replacement of soap noodles by water-containing fillers by utilizing hydrogel, and also provides a new method of introducing hydrogel phase material to process with soap noodle to make low TFM composition bars. Generally, fillers are materials that can replace soap in a soap bar without adversely affecting the cleansing property of the soap bar. The present invention utilizes hydrogel as a filler. A hydrogel is a gel which contains water but is not soluble in water. For example, when water is put on top of a hydrogel, the hydrogel and the water are clearly separated into two phases. Preferably, this hydrogel phase material is a three dimensional, metal-ions-caused, physically cross-linked network formed by polymer gelling agents, preferably polysaccharides or derivatives thereof. Preferably, the gelling agent is hydrophilic polymeric material that can form a three dimensional, physically cross-linked structure. Preferably the physical cross-link is thermoreversible such that the gelling is thermoreversible. Although hydrogel particles can be made by chemical cross-linking polymeric material, such as poly (2-hydroxyethyl methacrylate), carboxylated methyl-starch, hydrolyzate of acrylonitrile-grafted starch, polyacrylamide, poly(acrylic acid) salt, hydrolyzate of vinyl acetate-methyl acrylate copolymer, polyoxyethylene, poly(vinyl pyrrolidone), polystyrene sulfonate, poly(vinyl alcohol), etc., by chemical reaction, radiation, or the like, the preferred physically cross-linked hydrogels, especially thermoreversible hydrogels, enable the hydrogels to be processed into particulate units of desirable physical and chemical property in the resulting soap bars.

The preferred polymeric gelling agent is a polysaccharide (which can include natural polysaccharides or derivatives thereof) that can be easily dissolved in water at suitable temperature and form hydrogel when cooled to a lower temperature, e.g., room temperature, in some cases through the use of cations. Suitable polysaccharide-related materials suitable for forming the hydrogel include carrageenan, konjac gum, agar/agarose, locust bean gum (carob gum), cassia gum, gellan gum, alginate, and combinations thereof.

A preferred gelling agent is carrageenan. Carrageenan is a high molecular weight linear polysaccharide comprising repeating galactose units and 3,6-anhydrogalactose (3,6 AG), both sulfated and non-sulfated, joined by alternating α-(1,3) and β-(1,4) glycosidic links. The main species of Rhodophyceae used in the commercial production of carrageenan include *Euchema cottonii* and *E. spinosum*. Generally the types of carrageenans include kappa, iota, and lambda, the molecular weight of the carrageenans is from $5\times10^4$ to $70\times10^4$ Dalton. Different types of carrageenans might form gels of different softness or toughness characteristics. Due to the better gelling property, Kappa and Iota carrageenans are more preferred, and Kappa carrageenan is even more preferred for forming hydrogels for the soap bar of the present invention. Carrageenans are available as stable sodium, potassium, and calcium salts or, most generally, as a mixture of these. All carrageenans are dispersible in cold water, and when heated above 80° C. they are completely dissolved. During cooling process Kappa and Iota carrageenans form double helix molecular structures cross-linked by potassium and calcium ions, forming a tridimensional gel-type network. It has been found that carrageenan has to be dispersed well before its solubilization to avoid the formation of lumps and to obtain its complete functionality. Carrageenan is preferably premixed with other dry ingredients, adding into cold liquid with agitation to solubize the carrageenan. To achieve the more preferred gelling/melting point, potassium is the most effective metal ion to modify the gelling/melting point of carrageenan.

It has been found that there is a synergetic interaction between selected polysaccharides and other small molecules to improve the gel properties, especially between carrageenan and konjac gum. A combination of carrageenan and konjac gum is a more preferred gelling material because they provide gels of especially suitable gelling strength and processing parameters conducive for easy processing, such as mixing and forming hydrogel particles of the desirable sizes. Preferably, the ratio of carrageenan to konjac gum in wt % is about 1:10 to 10:1, more preferably about 6:4 to 4:6. With such preferred ranges, the resultant hydrogel can contain a large amount of water, is easily processed, and yet produces particulates of desirable sizes in the soap bar. It was found that higher gel rigidity improves the breaking up of the hydrogel chunks to form smaller particles as the soap mix is being mixed. Thus, the synergistic interaction of carrageenan and konjac improves gel strength and leads to smaller particles which reduce the grainy feeling of the resultant soap bar. Konjac contains the konjac mannan in their tubers. Konjac mannan is a heteropolysaccharide consisting of β-D-glucose (G) and β-D-mannose (M), with a G/M ratio of 1 to 3. The typical average range of konjac's molecular weight is $0.1\times10^5$ to $10\times10^6$ Dalton. The primary gelling agent or polysaccharide (such as carrageenan) builds up the three-dimensional cross-linked network to hold the structure and bind water. Any synergistic interaction with the three dimensional cross-linked network by other polymers (such as konjac) that can be used to enhance the structure or increase the water retention capability can be used for the formation of hydrogel. Similar to the synergetic interaction between carrageenan and other gums, locust bean gum (carob gum) or konjac gum or selected polyols can be used to help improve the hydrogel water retention capability.

It is desirable that the hydrogel particles are small enough that they do not produce a sensation of roughness to the consumers and small enough to allow beneficial material, such as glycerin or fragrance enclosed in the hydrogel particles to be released. It is desired that 95% (by number %, not wt %) of the diameter of the hydrogel particles is in the range of about 1 μm to 200 μm, more preferably about 5 μm to 100 μm, more preferably 5 μm to 60 μm. Generally in soap bars, once the particle size is smaller than 60 μm, it will not be noticeable in daily use for consumers. If the particle size is larger than 60 μm, the consumer will be able to notice the particles. If the particles are hard, such as certain inorganic fillers, talc, calcite and so on, they will result in a highly undesirable grittiness feel to consumers. If the particles are soft or elastic, they provide a massaging function, which is considered pleasurable to some consumers. The present invention also provides a robust formulation design with a wide range of particle size distribution. It is contemplated that the polysaccharides can be modified to form derivatives slightly different from the natural polymers and still retain significant water binding ability. The polysaccharide can be modified, e.g., to form hydroxyalkyl (e.g., hydroxypropyl) derivatives, cationic derivatives, and the like. Methods of making hydroxyalkyl and cationic polymers from polysaccharides are known in the art.

To allow the hydrogel phase particles to form well, in one aspect, it is preferred that the hydrogel is a thermoreversible gel. In thermoreversible gels, the gel network is a physically cross-linked network in which the physical cross-links can be disrupted by heat therefore allowing the gel to melt and yet to re-gel again when the heat is removed, rather than a network chemically cross-linked by covalent bonds. Other than carrageenan, konjac, and agar, other thermoreversible gels, such as synthetic materials can also be used. U.S. Pat. No. 5,306,501 is an example illustrating thermoreversible polyoxyalkylene block copolymers. The thermoreversible gel is advantageous because the hydrogel solution can be charged into a mixer and allowed to form a gel that is easy to break into chunks and particles. The hydrogel is dispersed among the soap noodle material and cools in the mixer to form a gel, which gets broken down into small pieces and particles. The hydrogel particles can be dispersed among the soap noodle material. On the contrary, nonthermoreversible covalently cross-linked gels are hard to break and therefore would have been hard to mix well with soap noodles.

Hydrogel particles of the present invention can be used to replace soap noodle to a significant amount. The hydrogel can be used at any percentage of the final soap formulation up to about 50 wt %, preferably about 5 wt % to 45 wt %, more preferably about 5 wt % to 35 wt %, and even more preferably about 5 wt % to 25 wt %. The preferred ranges of hydrogel amount result in soap bars that are relatively easy to process and produce desirable cleansing property. In terms of water content in the finished soap bar, the finished soap bar generally contains 15 wt % to 50 wt %, preferably 15 wt % to 30 wt %, preferably 15 wt % or more, more preferably 20 wt % to 25 wt % of water. In terms of the amount of hydrogel content in the soap bar, the gelling material (such as a polysaccharide such as Kappa carrageenan, or a combination of gellants) constitutes preferably about 0.05 wt % to 10 wt %, more preferably about 0.1 wt % to about 5 wt % of the soap bar.

The inclusion of hydrogel phase material in the soap bar provides advantages over soap bars in which the gelling material is not a hydrogel that gels from a true hydrogel solution, not merely swollen gelling particles. In the hydrogel phase particulates of the present invention, included constituents are incorporated into the hydrogel solution when the gel is made before the hydrogel is broken up into particulate units. Thus, the included constituents are more evenly distributed in the hydrogel particles and do not easily leach out of the hydrogel particles during the soap-bar-making process, even under pressure or in an elevated temperature, such as those present in the mixing, milling, extruding and stamping processes. This significantly reduces the loss of fragrance during process (if fragrance is included), reduces the viscosity to allow easier mixing if glycerin in included, and facilitates mixing and the breaking of hydrogel chunks into smaller particulates if talc or other inorganic powdery materials are included in the hydrogel.

In the present invention, the hydrogel is made to include a large amount of water when it is mixed with the soap noodle in an amalgamator or mixer. Since the hydrogel is made by dissolving in hot water and then gelled, it is a hydrogel with a cross-linked network binding water in a more or less uniform fashion over the whole gel. Particles formed from this hydrogel can therefore be formed coreless. In fact, as the hydrogel particles become affixed in the soap bar, some of the water from the hydrogel may become lost to the soap base and to the atmosphere, the concentration of water at the inner or more central part of the hydrogel particle is no less than that at the more peripheral part of the hydrogel. Hydrogel constituents such as talc, humectant, certain fragrance, etc., that do not cross the hydrogel phase into the soap base or leave the hydrogel particle easily, would remain at a relatively uniform concentration in the hydrogel bulk even if the hydrogel containing soap bar is placed in commercial storage in a stable condition for a period of time. Thus, the hydrogel particles are unlike gelling particles that are simply mixed in the soap mix or in a liquid with wetting the gelling material. Gelling particles if merely dispersed in the soap base mixed with water or dispersed in an aqueous solution or water to absorb water without dissolving will simply swell. Such swelling requires water to slowly migrate into a dry core. Thus, the gelling material will form a swollen particle with a core that has less water than the peripheral part of the particle. In some cases, the core may never even become hydrated since the peripheral part of the particle impedes water penetration and water does not diffuse into dry material. Thus, the outer part of the swollen particle may be very wet but the inside may be dry. Such swollen particles if formed by absorbing an aqueous solution via dispersing the gelling agent in an aqueous solution may lose a significant amount of the aqueous solution original held in the swollen particles when the swollen particles are placed under pressure causing the soap mix (i.e., the material that includes soap base and hydrogel that is being mixed) to become soft or mushy during processing, as when the soap mix is processed through milling, extruding and stamping, etc. Thus, excipients such as vitamins, fragrance, etc., that are originally absorbed into the gelling material during wetting by the aqueous solution can easily be lost during processing of the soap mix into a soap bar.

In the formation of certain hydrogel particles, such as from carrageenan material, waiting for the hydrogel solution to start to gel before mixing into the soap noodle base allows the hydrogel to form into phase chunks and particles to be mixed with the soap base in the mixer rather than as a mixture of water and gelling material particles.

Comparing with the traditional soap finishing process, in the present invention, only an extra pre-mixer is needed for making hydrogel solution. The following indicates a set of general steps for a modified soap finishing process. To make a thermoreversible hydrogel, water is put into a pre-mixer, and gelling agent (e.g. polysaccharides such as carrageenan and konjac gum) and other additives (e.g., talc and glycerin) are added into the water, and the material is agitated and heated (for example, to about 90° C.). The relevant salts (e.g., KCl for carrageenan), if needed, are then added to the mixture solution. The mixture solution is then cooked for a period of time, e.g., 4-10 minutes to ensure that the gelling material is dissolved well to form a homogenous solution mixture. Insoluble materials such as talc, if included, may be present in the hydrogel solution mixture. Preferably such insoluble materials are also relatively well mixed in the solution such that when made into particles, the insoluble materials particles will be distributed substantially uniform in a particle. At this time, the hydrogel solution is charged into a mixer to be mixed with soap noodle and other additives immediately. As the hydrogel solution gels as it is being mixed by agitators with the soap noodle and other additives, it becomes well dispersed among the soap noodle material and forms the hydrogel particles in-situ when the temperature drops during the mixing, the larger pieces and chunks of hydrogel are broken into smaller pieces. The hydrogel phase particles will eventually become embedded in the soap matrix after a soap bar is formed.

Figure 2:
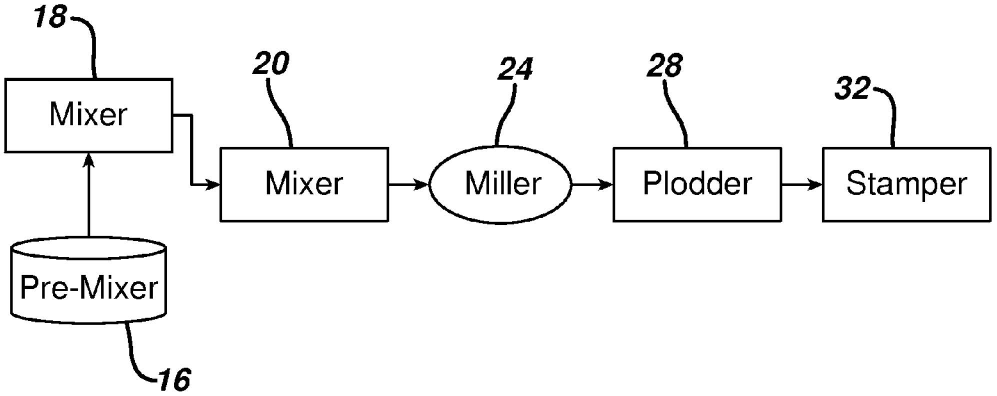
FIG. 2 is a flow chart illustrating a typical process for making solid soap bars according to the present invention.

The mixed material is then processed further by other processing steps such as milling, extruding and stamping, etc. FIG. 2 illustrates a flow chart of a typical process of the present invention. The illustrative process includes premixing the hydrogel agent with ingredient materials and water in a heated pre-mixer 16. The premixed material is charged into a mixer 18 and mixed with soap noodles. The mixed material is then further processed in a refiner 20, miller 24, plodder 28, and a stamper 32, which are well known soap making machines. Generally, the material is mixed by extrusion through orifices in a refiner, extruded into thin sheets in a miller, and extruded into solid soap rods in a plodder. The soap rod is cut and stamped into soap bars. Through this process, the material becomes well mixed in the soap base mix and particulate ingredients in the soap base mix are dispersed and well distributed in the resultant soap bar.

In a simple form, the soap making method of the present invention will not require great changes the traditional soap finishing process, but merely the inclusion of a simple preheating pre-mixer vessel for making the hydrogel solution. Using the hydrogel as the soap noodle replacement, the replacement percentage range can be achieved up to 45 wt % based on formulation, preferably up to 35 wt %. To make sure the polysaccharides solution can form gels that can act as the solid filler, the gel strength and gelling point can be control for effective processing. Metal cations, polyols and synergetic interaction between polysaccharides can be used to facilitate the hydrogel formation for this invention.

It is contemplated that the hydrogel solution can be formed into small particles before being mixed with the soap noodles. It is contemplated that the hydrogel solution can be sprayed or spun into droplets to mix with soap noodles, thereby forming hydrogel phase particles in the soap base mix. It is further contemplated that the hydrogel can gel and broken up into particles before mixing into with the soap noodles.

Apart from thermoreversible gels, other polysaccharide gels or their derivatives that can form hydrogels can also be used to form soap bars of the present invention. For example, alginate, gellan gum, carob gum, and the like, can be made to gel by interacting with certain cations. For example, alginate or gellan gum can be made to gel by introduction of calcium ions and carob gum can be made to gel at about pH 5.5 to 7 in the presence of sodium borate. By using the appropriate amount of the cations in relation to a suitable amount of gelling material and water, gelling can be controlled so that as the gel solution is gelling, the gelling solution is charged into the mixer to be mixed with the soap base to form the soap mix. Such gels are cross-linked by physical interactions with the aid of ions, which can be controlled easier and therefore more preferred than covalently cross-linked gels. For example, the gelling of the gellan gum can be controlled by the amount of cations added and the temperature. Thus, the cross-linking in the cation controlled hydrogels, e.g., gellan gum, alginate, etc., are based on the physical interference between strands of the gellant polymer, rather than by covalent bonds. As the hydrogel is formed and broken down by mixing and agitation, hydrogel particles of the right dimensions can be made.

Many different ingredients can be advantageously used in the hydrogel particles. Suitable materials can be solid, liquid, semi-liquid, etc., and can be hydrophilic or even hydrophobic. For a hydrophobic material, dispersing aids such as emulsifiers can be used to interact with various ingredients so as to allow even distribution of the ingredients in the hydrogel. Flavor and fragrances, such as those traditionally known in the art, can be incorporated into the hydrogel by use of gelling agents. Dispersing aids, emulsifiers, etc., and other aids for aiding the incorporation of hydrophobic materials, such as fragrance oils, are known in the art and widely used for flavor release technology. Making use of different gelling mechanisms and interactions with the flavoring compounds, the flavor release can be easily controlled. For example, by controlling the hydrogel particle size, the hardness of the gel, the water content, the emulsifying system, etc., the release of the flavor or fragrance can be controlled in the soap design. With the benefit of the present invention disclosure, fragrance release benefit can be easily achieved using hydrogel particles.

Another useful ingredient in the hydrogel is processing aid, such as inorganic powdery material, e.g., talc, calcite, kaolin, silicon dioxide, titanium dioxide, diatomaceous earth, etc. We found that such inorganic powdery material included in the hydrogel facilitates the breaking up of the hydrogel in the mixing process with the soap noodles so that hydrogel particles can be made into particles of suitable sizes with high efficiency. Talc, calcite and kaolin are preferred material. An even more preferred inorganic powdery materials are talc and calcite. Generally, the inorganic powdery material is added to make the hydrogel solution in the range of a weight percentage of inorganic powdery material to hydrogel of 1.0 wt % to 40 wt %, more preferably from about 2.0 wt % to 30%, and even more preferably about 5 wt % to about 25 wt % of the hydrogel. Preferably the inorganic powdery material in the soap bar is about 0.05 wt % to 16 wt %, more preferably from about 0.1 wt % to 12 wt %, and more preferably about 0.25 wt % to about 10 wt %. Generally, the particle size of the inorganic powdery material is higher than about 200 meshes.

Water is major component of the hydrogel phase particles. Preferably, more water is contained in the hydrogel phase particles than in the soap base material outside of the hydrogels. Preferably, most of the water that is in the resultant soap bar is in the hydrogel phase particles and there is less, preferably very little water in the soap bar outside of the hydrogel phase particles. Preferably, more than 90% of the water is in the hydrogel particles. In this way, the hydrogel, containing an amount of water and acting as fillers, will interfere less with the soap noodle mixing than the equivalent amount of free water directly in the soap base mix. In the hydrogel phase particles, preferably water constitutes more than about 50 wt %, more preferably about 50 wt-90 wt %, more preferably about 50 wt % to 75 wt %. It has been found that after the hydrogel solution has been charged into the mixer and the soap base mix processed into soap bars, the weight loss due to water evaporation is less than about 2.0% of the water present in the formulation. It has been found that the water that is in the hydrogel phase does not migrate rapidly out of the hydrogel particles into the soap matrix material rapidly with time. Thus, as observable by average consumers, the soap bar does not become wet or mushy in storage under normal ambient room condition. Soap noodles themselves sometimes contain a little water, such as about 8 wt % to 15 wt %. Thus, knowing the approximate water content of the soap noodle, the water content of the soap bar after manufacture can be estimated, and can also be determined by experiments, such as by removing all the water by evaporation.

The hydrogel phase can optionally further contain a humectant. Humectants can be selected from the group consisting of polyhydric alcohols (polyols), water soluble alkoxylated nonionic polymers, and mixtures thereof. The humectants contained in the hydrogel can be used at levels of the composition from about 0.1 wt % to 30 wt %, more preferably from about 0.5 wt % to 25%, and more preferably about 5% to about 20% of the hydrogel. Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, and mixtures thereof. Water soluble alkoxylated nonionic polymers such as polyethylene glycols and polypropylene glycols are useful as well. A particularly useful humectant is glycerin. Humectants can benefit users as moisturizers when contacting the skin.

It is noted that it is a well known facts that humectants, such as glycerin, glycols, etc., that are viscous liquids tend stick to other materials to make the mixing process difficult to control if present in the material being mixed. Thus, if gelling material and humectants are directly mixed with soap noodles and water, the mixing material tends to become highly viscous and difficult to handle. For the present invention, in which the humectant(s) are included in the hydrogel instead of being present in substantial quantity in the soap base mix material, the viscosity of the mixing material is reduced substantially compared to having the humectants in the soap base directly. The humectant, e.g., glycerin, can be present in the hydrogel in an amount of 0.1 wt % to 60 wt %, more preferably from about 5 wt % to 50 wt %, and even more preferably about 10 wt % to about 40 wt % of the hydrogel.

It is noted that surfactants also can be added into the hydrogel filler to further improve the lathering properties and skin feeling during use. The synthetic surfactants can be used in this invention include anionic, amphoteric, nonionic, zwitterionic, and cationic surfactants. Synthetic surfactants can generally be used in the present hydrogel filler at a level of from 0.1 wt % to about 40 wt % in hydrogel filler, preferably from about 0.5 wt % to about 20 wt %.

Examples of anionic surfactants include but are not limited to alkyl sulfates, anionic acylsarcosinates, methyl acryl taurates, N-acyl glutamates, acyl isethionates, alkyl ether sulfates, alkyl sulfosuccinates, alkyl phosphate esters, ethoxylated alkyl phosphate esters, trideceth sulfates, protein condensates, mixtures of ethoxylated alkyl sulfates and the like. Alkyl chains for these surfactants are C8-C22, preferably C10-C18. Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, for example, carboxy, sulfate, sulfonate, phosphate, or phosphonate. Examples include: 4-[N,N-di(2-hydroxyethyl)-N-octadecylammonio]-butane-1-carboxylate; 3-[N,N-dipropyl-N-3-dodecoxy-2-hydroxypropylammonio]-propane-1-phosphonate. Examples of amphoteric surfactants which can be used in the hydrogel filler are those which can be broadly described as derivatives of aliphatic secondary and tertiary amines in which the aliphatic radical can be straight chain or branched and wherein one of the aliphatic substituents contains from 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate; N-alkyltaurines, such as the one prepared by the reacting dodecylamine with sodium isethionate according to the teaching of U.S. Pat. No. 2,658,072; N-higher alkyl aspartic acids, such as those produced according to the teaching of U.S. Pat. No. 2,438,091. Other amphoterics such as betaines are also useful in the hydrogel filler. Examples of betaines useful herein include the high alkyl betaines such as coco dimethyl carboxymethyl betaines, lauryl dimethyl carboxy-methyl betaine, lauryl dimethyl alpha-carboxyethyl betaine, cetyl dimethyl carboxymethyl betaine, lauryl bis-(2-hydroxylethyl)carboxymethyl betaine, stearyl bis-(2-hydroxylpropyl)carboxymethyl betaine, oleyl dimethyl gamma-carboxypropyl betaine, and the like. Examples of suitable cationic surfactants include stearyldimethylbenzyl ammonium chloride; dodecyltrimethylammonium chloride; nonylbenzylethyldimethyl ammonium nitrate; tetradecylpyridinium bromide; laurylpyridinium chloride; cetylpyridinium chloride; luarylpyridinium chloride; laurylisoquinolium bromide; dilauryldimethyl ammonium chloride; and stearalkonium chloride; and other cationic surfactants known in the art. Nonionic surfactants used in the hyrdogel filler can be broadly defined as compounds produced by the condensation of alkylene oxide groups (hydrophilic in nature) with an organic hydrophobic compound, which many be aliphatic or alkyl aromatic in nature.

The hydrogel filler can optionally contain other beneficial agents, including hydrophilic and/or hydrophobic beneficial agents. Beneficial agents include other polyols, vitamins, drugs, nutrients, permeation enhancers, colorants, sunblocks, anti-bacterial ingredients, etc. Many of such beneficial agents are well known and commercially available. Further, in the soap bar, external to the hydrogel filler particles, many optional materials can also be included. Beneficial agents, surfactants, salts, fatty acids, structurants, other fillers (such as inorganic fillers), colorants, fragrance, processing aids, etc., as known to those skilled in the art, and can also be included as such optional material in the soap bar. If needed, the pH range of the hydrogel can be adjusted to be compatible with some of the beneficial agents.

The following examples illustrate the soap bars that can be formed with the present invention. All percentages are wt % unless clearly specified otherwise in the content.

EXAMPLE 1

The following method was used in making soap bars: Charge the amount of water and sorbitol according to the formula into the pre-mixer, stir at room temperature, and add the talc (or calcite or other powdery material) into the pre-mixer. Stir the material in the pre-mixer at 500-600 rpm for a few minutes to disperse the ingredients evenly. Heat the solution to 50-60° C., add the carrageenan into the solution, increase the stirring speed to 800 rpm, continue to heat the solution to 85° C., and maintain the temperature until the carrageenan is totally dissolved. Then add the KCl to the solution and keep the temperature for a few minutes to totally dissolve the KCl. Charge the soap noodle and other additives into a double sigma mixer to mix for a few minutes until the soap noodle is totally broken down to very small powdery form, then charge the hot hydrogel solution into the double sigma mixer once the solution is ready. Mix them for a few minutes and charge them into the refining machine and follow by milling, extruding, extruding, and stamping.

TABLE 1

Soap bar formulations with carrageenan hydrogel fillers (contents in wt %)

| Ingredients | Control | 1 | 2 | 3 | 4 | 5 | 6 |
|---|---|---|---|---|---|---|---|
| Soap noodle | 98.70 | 83.26 | 77.96 | 77.30 | 80.16 | 80.16 | 80.16 |
| Titanium Dioxide | 0.20 | 0.20 | 0.20 | 0.20 | 0.3 | 0.3 | 0.3 |
| EDTA | 0.1 | 0.10 | 0.10 | 0.10 | 0.1 | 0.1 | 0.1 |
| Fragrance | 1.0 | 1.00 | 1.00 | 1.00 | 1.0 | 1.0 | 1.0 |
| Carrageenan | — | 0.27 | 0.37 | 0.70 | 0.27 | 0.27 | 0.27 |
| KCl | — | 0.17 | 0.37 | 0.70 | 0.17 | 0.17 | 0.17 |
| Talc | — | 2.50 | 2.50 | — | 3.0 | | 0 |
| Calcite | — | — | — | — | — | 3.0 | 3.0 |
| Sorbitol | — | — | — | — | 5.0 | 5.0 | 5.0 |
| Surfactant | — | — | — | — | — | — | 1.5 |
| Water | — | 12.50 | 17.50 | 20.00 | 10.0 | 10.0 | 8.5 |
| Hydrogel Dosage | 0 | 15.44 | 20.74 | 21.40 | 18.44 | 18.44 | 18.44 |
| Gel Break Strength g/cm$^2$ | — | 2266 | 2089 | 4825 | 1342 | 2320 | 1431 |
| Gelling Point/° C. | — | 68 ± 2 | 75 ± 2 | 92 ± 2 | 72 ± 2 | 82 ± 2 | 74 ± 2 |

Table 1 shows the characteristics of milled soap bars made with the above described process. The carrageenan used in these examples was kappa-carrageenan, code name E407, obtained from Shanghai Brilliant Gum Co., Ltd. In Table 1, the hydrogels were formed from water, carrageenan and KCl and in some cases included talc as an ingredient. For comparison, a control bar was made of soap noodles (98.7 wt %), EDTA, fragrance, and 0.2 wt % titanium dioxide without any other filler material. The hydrogel soap bars all contained the same wt % in relation to the soap bar formulation of EDTA and fragrance as the control, and either 0.2 wt % or 0.3 wt % of titanium oxide present in the base mix (i.e., the base material that does not have hydrogel fillers). The gel strength was measured using the Standard test method used in food industry using a TA.XTPIus Texture Analyzer with a 0.5 inch (1.27 cm) Radius Cylinder (P/0.5R) Cylinder probe. The international standard test method named ISO 9665: 1998(E) can be used with the following settings: test mode is compression, pre-test speed is 0.5 mm/sec, test speed is 0.5 mm/sec, post-test speed is 0.5 mm/sec, target mode is distance, trigger type is force, trigger force is 5 g. Said ISO 9665: 1998(E) testing method, as described in International Method—Adhesives-Animal Glues—Methods of Sampling and Testing, ISO 9665, Second Edition (1998-09-15) is herein incorporated by reference. All gel strength measurements in this application were done with this method. The gelling point was tested by the following method: Put the polysaccharide solution into a 95° C. water bath to make sure the solution would not form a gel. Control the temperature decreasing rate of the water batch at 1° C./min, and record the temperature when the solution forms the hydrogel. We were able to incorporate from about 10 to 20 wt % of water into the soap formulation and form stable soap bars with the traditional mixing, refining, milling, extruding, and stamping processes.

TABLE 2

Performance results of soap bars of Table 1

| Parameters | Control | 1 | 2 | 3 | 4 | 5 | 6 |
|---|---|---|---|---|---|---|---|
| Foam Volume/cm | 21.0 | 22.0 | 21.8 | 22.0 | 21.0 | 21.3 | 21.0 |

Table 2 shows the foaming performance of the soap bars of Table 1. The forming method used was the Ross-Mile test method (ISO696-1975 or GB7462-87) at soap concentration of 0.5 g/L and a water hardness of 150 ppm. The same method was used in all foaming performance tests in this application. It is generally accepted by skilled artisans in soap technology that foaming performance (foam volume/cm) is a representation of the cleansing property of a soap bar. Table 2 shows that the soap bars of Table 1 have similar cleansing property. Thus, the soap bars that contain a large amount of water in hydrogel fillers performed similarly well as the control bar that did not contain any water containing filler.

TABLE 3

Soap bar formulations with hydrogel fillers formed by carrageenan/konjac (contents in wt %)

| Ingredients | 7 | 8 | 9 | 10 | 11 | 12 | 13 | 14[a] |
|---|---|---|---|---|---|---|---|---|
| Soap noodle | 87.81 | 82.67 | 77.99 | 77.67 | 72.97 | 67.97 | 67.97 | 62.90 |
| Titanium Dioxide | 0.30 | 0.30 | 0.20 | 0.30 | 0.30 | 0.30 | 0.30 | 0.30 |
| EDTA | 0.10 | 0.10 | 0.10 | 0.10 | 0.10 | 0.10 | 0.10 | 0.10 |
| Fragrance | 1.00 | 1.00 | 1.00 | 1.00 | 1.00 | 1.00 | 1.00 | 1.00 |
| Carrageenan | 0.11 | 0.16 | 0.19 | 0.16 | 0.27 | 0.27 | 0.27 | 0.30 |
| Konjac | 0.09 | 0.14 | 0.18 | 0.14 | 0.18 | 0.18 | 0.18 | 0.20 |
| KCl | 0.09 | 0.14 | 0.35 | 0.14 | 0.18 | 0.18 | 0.18 | 0.20 |
| Talc | — | — | 2.50 | — | — | 5.00 | — | 10.0 |
| Sorbitol | — | — | — | 5.00 | — | — | — | 10.0 |
| Glycerin | 0.50 | 0.50 | — | 0.50 | 10.00 | 10.00 | 12.50 | — |
| Water | 10.00 | 15.00 | 17.50 | 15.00 | 15.00 | 15.00 | 17.50 | 15.00 |
| Hydrogel Dosage | 10.80 | 16.00 | 20.80 | 20.40 | 25.60 | 30.60 | 30.60 | 35.70 |
| Gel Break Strength ($g/cm^2$) | 4252 | 4252 | — | 3842 | 3079 | 2402 | 670 | — |
| Gelling Point/° C. | 63 ± 2 | 63 ± 2 | — | 67 ± 2 | 82 ± 2 | 85 ± 2 | 80 ± 2 | — |

[a]The hydrogel solution of this Number 14 example was very viscous and paste-like. It gelled very quickly during the transferring from the glass beaker into the container. The gel formed before it could be put into the container. So the gel strength and gelling point were not tested by the test methods we used for measuring these two parameters in the other samples.

Table 3 shows the formulations of soap bars that contain hydrogel phase fillers made from carrageenan, konjac, KCl, and water and include ingredients selected from glycerin, sorbitol and talc. The hydrogel dosage varied from about 11 wt % to 36 wt % in the formulation and the amount of water in the hydrogel fillers varied from about 10 wt % to 17.5 wt %. The soap noodle content varied from 63 wt % to 88 wt %.

It was observed that in general, the higher the gelling point of the hydrogel, the sooner the polysaccharides solution will form the hydrogel phase during mixing with soap noodles. Thus, higher water retention during mixing with soap noodle for hydrogel can be achieved. Preferably, the soap bars of the present invention are made from hydrogels that have a gelling temperature of about 35° C. to 95° C., more preferably 45° C. to 85° C. Also, it was observed that the higher gel strength the hydrogel, the higher the water retention capability that can be achieved. Preferably, the soap bars of the present invention are made from hydrogels that have gel strength of 200 $g/cm^2$ to 15000 $g/cm^2$, more preferably 600 $g/cm^2$ to 6500 $g/cm^2$.

TABLE 4

Performance results of the soap bars of Table 3

| Parameters | 7 | 8 | 9 | 10 | 11 | 12 | 13 | 14 |
|---|---|---|---|---|---|---|---|---|
| Foam Volume/cm | 21.5 | 21.0 | 21.0 | 21.0 | 21.4 | 21.2 | 21.4 | 21.4 |

Table 4 shows the foaming performance of the soap bars of Table 3. The forming method used was the Ross-Mile test method at soap concentration of 0.5 g/L at a water hardness of 150 ppm. Table 2 and Table 4 show that the soap bars of the two tables have similar cleansing property. Thus, the soap bars that contain a large amount of water in hydrogel fillers performed similarly well as the control bar that did not contain any water containing filler.

TABLE 5

Soap bar formulations with agar hydrogel fillers (contents in wt %)

| Ingredients | 15 | 16 | 17 | 18 |
|---|---|---|---|---|
| Soap noodle | 85.94 | 80.83 | 74.90 | 69.90 |
| Titanium Dioxide | 0.20 | 0.20 | 0.20 | 0.20 |

TABLE 5-continued

Soap bar formulations with agar hydrogel fillers (contents in wt %)

| Ingredients | 15 | 16 | 17 | 18 |
|---|---|---|---|---|
| EDTA | 0.10 | 0.10 | 0.10 | 0.10 |
| Fragrance | 1.00 | 1.00 | 1.00 | 1.00 |
| Agar | 0.26 | 0.37 | 0.80 | 0.80 |
| Sorbitol | — | — | 5.50 | 5.50 |
| Talc | — | — | — | 5.00 |
| Water | 12.50 | 17.50 | 17.50 | 17.50 |

TABLE 5-continued

| Soap bar formulations with agar hydrogel fillers (contents in wt %) | | | | |
|---|---|---|---|---|
| Ingredients | 15 | 16 | 17 | 18 |
| Hydrogel Dosage | 12.76 | 17.87 | 23.8 | 29.0 |
| Gel Break Strength g/$cm^2$ | 1086 | 1086 | 831 | 1886 |
| Gelling Point/° C. | 43 ± 2 | 43 ± 2 | 50 ± 2 | 70 ± 2 |

Table 5 shows the formulations of hydrogel soap bar made from agar. Agar is a strongly gelling hydrocolloid from marine algae. Its main structure is chemically characterized by repetitive units of D-galactose and 3,6-anhydro-L-galactose, with few variations, and also a low content of sulfate esters. Useful molecular weight of agar is from $1\times10^4$ to $5\times10^6$ Dalton. The agar used in these examples was obtained from Shanghai Brilliant Gum Co., Ltd, with a code name BLR6001. The hydrogel dosage varied from 13 wt % to 29 wt %. The water content in the hydrogel varied from about 12.5 wt % to 17.5 wt % of the soap bar formulation material.

TABLE 6

| Performance results of soap bars of Table 5 | | | | | |
|---|---|---|---|---|---|
| Parameters | Glycerin Bar[a] | 15 | 16 | 17 | 18 |
| Foam Volume/cm | 21.0 | 21.8 | 22.2 | 21.6 | 19.8 |

[a]The Glycerin Bar was a Savlon Bar with aloe vera (a soap product of Johnson & Johnson for India market, made by VVF limited, ingredients: sodium palmate, sodium palm kernelate, glycerin, water, fragrance, triclosan, *Aloe Barbadensis* Leaf Extract, CI 74260, CI 11680)

Table 6 shows the foaming performance of the soap bars of Table 5 and a commercial glycerin bar. Table 2 and Table 6 show that the soap bars of the two Tables have similar cleansing property. Thus, the soap bars that contained a large amount of water in agar hydrogel fillers performed similarly well as the control bar and the SAVLON glycerin bar that did not contain any water containing filler. Further, comparing Table 4 and Table 6 shows that glycerin bars can be made according to the present invention with hydrogel fillers that perform similarly with nonhydrogel commercial glycerin bars.

TABLE 7

| Soap bar formulations with sodium alginate hydrogel fillers (contents in wt %) | | |
|---|---|---|
| Ingredients | 19 | 20 |
| Soap noodle | 85.94 | 80.58 |
| Titanium Dioxide | 0.20 | 0.20 |
| EDTA | 0.10 | 0.10 |
| Fragrance | 1.00 | 1.00 |
| Sodium Alginate | 0.26 | 0.35 |
| EDTA | — | 0.17 |
| $CaCl_2$ | 0.00 | 0.1 |
| Water | 12.50 | 17.50 |
| Hydrogel Dosage | 12.76 | 18.12 |

Table 7 shows the formulations of hydrogel soap bar made from sodium alginate, which is not thermoreversible. The hydrogel dosage varied from 13 wt % to 18 wt %. The water content in the hydrogel varied from about 12.5 wt % to 17.5 wt % of the soap bar formulation material. Alginate is a family of unbranched binary copolymers of (1→4) linked β-D-mannuronic acid (M) and α-L-guluronic acid (G) residues of widely varying composition and sequence with a molecular weight range from $3\times10^4$ to $1\times10^6$ Dalton. For example, the commercial alginates produced from *Laminaria hyperborean, Macrocystis pyrifera, Laminaria digitata, Ascophyllum nodosum, Laminaria japonica, Eclonia maxima, Lessonia nigrescens, Durvillea Antarctica* and *Sargassum* can be used for the soap bars of this invention. For the hydrogel formed by alginate without $CaCl_2$, as an illustration, the 0.26 wt % alginate was dispersed into the 12.5 wt % water, and the resulting solution was heated to 80° C. The solution was stirred continually at 800 rpm for adequate time until the alginate was totally dissolved. The solution was cooled to room temperature, at which point the solution formed a highly viscous paste and was charged into the mixer and mixed it with soap noodle and other ingredients. For the hydrogel formed by alginate with $CaCl_2$, the 0.10 wt % $CaCl_2$ and 0.17 wt % EDTA were dissolved into a 1 wt % water portion, and the 0.35 wt % alginate was dissolved into a 16.5 wt % water portion to form the solutions containing the 17.5 wt % water. The alginate solution was heated to 60° C. The $CaCl_2$/EDTA solution was added into the alginate solution slowly to ensure that the hydrogel can be formed properly. After the hydrogel solution has been formed, it was cooled to room temperature and charged into the mixer and mixed it with soap noodle and other ingredients.

TABLE 8

| Performance results of soap bars of Table 7 | | |
|---|---|---|
| Parameters | 19 | 20 |
| Foam Volume/cm | 21.8 | 21.0 |

Table 8 shows that the soap bars that contained a large amount of water in sodium alginate hydrogel fillers performed similarly well as the control bar.

TABLE 9

| Soap bar formulations with gellan gum hydrogel fillers (contents in wt %) | | |
|---|---|---|
| Ingredients | 21 | 22 |
| Soap noodle | 85.91 | 83.14 |
| Titanium Dioxide | 0.20 | 0.20 |
| EDTA | 0.10 | 0.10 |
| Fragrance | 1.00 | 1.00 |
| Gellan Gum | 0.26 (LA) | 0.38 (LA:HA = 1:1)[a] |
| $CaCl_2$ | 0.03 | 0.18 |
| Water | 12.50 | 15.00 |
| Hydrogel Dosage | 12.79 | 15.56 |
| Gel Break Strength g/$cm^2$ | 4441 | 656 |

[a]LA means low acyl gellan gum, HA means high acyl gellan gum, LA:HA = 1:1 means the weight ratio of LA to HA is 1:1.

Table 9 shows the formulations of hydrogel soap bar made from gellan gum, which is not thermoreversible. The hydrogel dosage varied from 13 wt % to 16 wt %. The water content in the hydrogel varied from about 12.5 wt % to 15 wt % of the soap bar formulation material. The gellan gum used was an extracellular polysaccharide secreted by the micro-organism *Sphingomonas elodea* previously referred to as *Pseudomonas elodea* with a molecular weight range from $3\times10^4$ to $2\times10^6$ Dalton. The primary structure of gellan gum used in this design is composed of a linear tetrasaccharide repeat unit: →3)-β-D-Glcp-(1→4)-β-D-GlcpA-(1→4)-β-D-Glcp-(1→4)-α-L-Rhap-(1→. The gellan gum was obtained from CP Kelco with a brand name KELCOGEL CG-HA for high acyl gellan gum and KELCOGEL CG-LA for low acyl gellan gum. The gellan gum hydrogel were made by the following process: The $CaCl_2$ was dissolved in de-ionized (DI) water to make a $CaCl_2$ solution, Gellan gum was added into DI water, and the dispersion was heated to 50-60° C. to dissolve the gellan gum. After the gellan gum was totally dissolved in the water, the $CaCl_2$ solution was added into the gellan gum solution, the solution was cooled to room temperature to form the hydrogel. The hydrogel was charged into the mixer and mixed with the soap noodle and other ingredients.

TABLE 10

Performance results of soap bars of Table 9

| Parameters | 21 | 22 |
|---|---|---|
| Foam Volume/cm | 21.6 | 21.6 |

Table 10 shows that the soap bars that contain a large amount of water in gellan gum hydrogel fillers perform similarly well as the control bar.

The practice of the present invention will employ, unless otherwise indicated, conventional methods used by those in soap product development within those of skill of the art. Embodiments of the present invention have been described with specificity. The embodiments are intended to be illustrative in all respects, rather than restrictive, of the present invention. It is to be understood that various combinations and permutations of various parts and components of the schemes disclosed herein can be implemented by one skilled in the art without departing from the scope of the present invention. Further, where a substance is described to comprise certain ingredients, it is contemplated that a substance in some cases can also be made consisting essentially of the ingredients. All patent documents cited herein are incorporated by reference in their entireties herein.

What is claimed is:

1. A solid soap comprising:

a solid phase soap base; and hydrogel phase particles embedded in said soap base, wherein said solid soap contains at least 15% by weight of water and is millable, wherein the hydrogel phase particles are formed from hydrogel with gelling point from 45° C. to 85° C. and with gel strength of 600 g/cm2 to 6500 g/cm2, and wherein the hydrogel phase particles are made using ingredients comprising carrageenan, a potassium salt and at least one material selected from the group consisting of konjac, polyhydric alcohols selected from the group consisting of glycerin, sorbitol, propylene glycol, butylene glycol, hexylene glycol, ethoxylated glucose, 1, 2- hexane diol, hexanetriol, dipropylene glycol, erythritol, trehalose, diglycerin, xylitol, maltitol, maltose, glucose and fructose, and an inorganic powdery materials comprising talc.

2. The solid soap of claim 1 wherein said potassium salt is potassium chloride.

3. The solid soap of claim 1 wherein the solid soap contains at least 15 wt % water and the hydrogel phase particles are coreless.

4. The solid soap of claim 1 wherein the solid soap contains at least 15 wt % water and the hydrogel phase particles containing at least 2 wt % of inorganic particles on the soap and more water is in the hydrogel phase particles than outside of the hydrogel phase particles.

5. The solid soap of claim 1 wherein the solid soap contains at least 15 wt % water and the hydrogel phase particles contain at least 2 wt % of talc on the soap, the hydrogel phase particles containing carrageenan and another polysaccharide.

6. The solid soap of claim 1 comprising less than 80 wt % fatty acid alkali salt or surfactant.

7. The solid soap of claim 1 wherein the hydrogel phase particle and the solid soap base have refractive indexes that are close such that the solid soap is transparent or translucent.

8. The solid soap of claim 1 wherein the hydrogel phase particles constitute 5 wt % to 50 wt % of the solid soap.

9. The composition of claim 1 wherein said solid soap contains from about 50 to 90% by weight of fatty acid alkali salts.

* * * * *